March 25, 1947. J. GAUJARD Plant Pat. 727
ROSE PLANT
Filed June 26, 1943
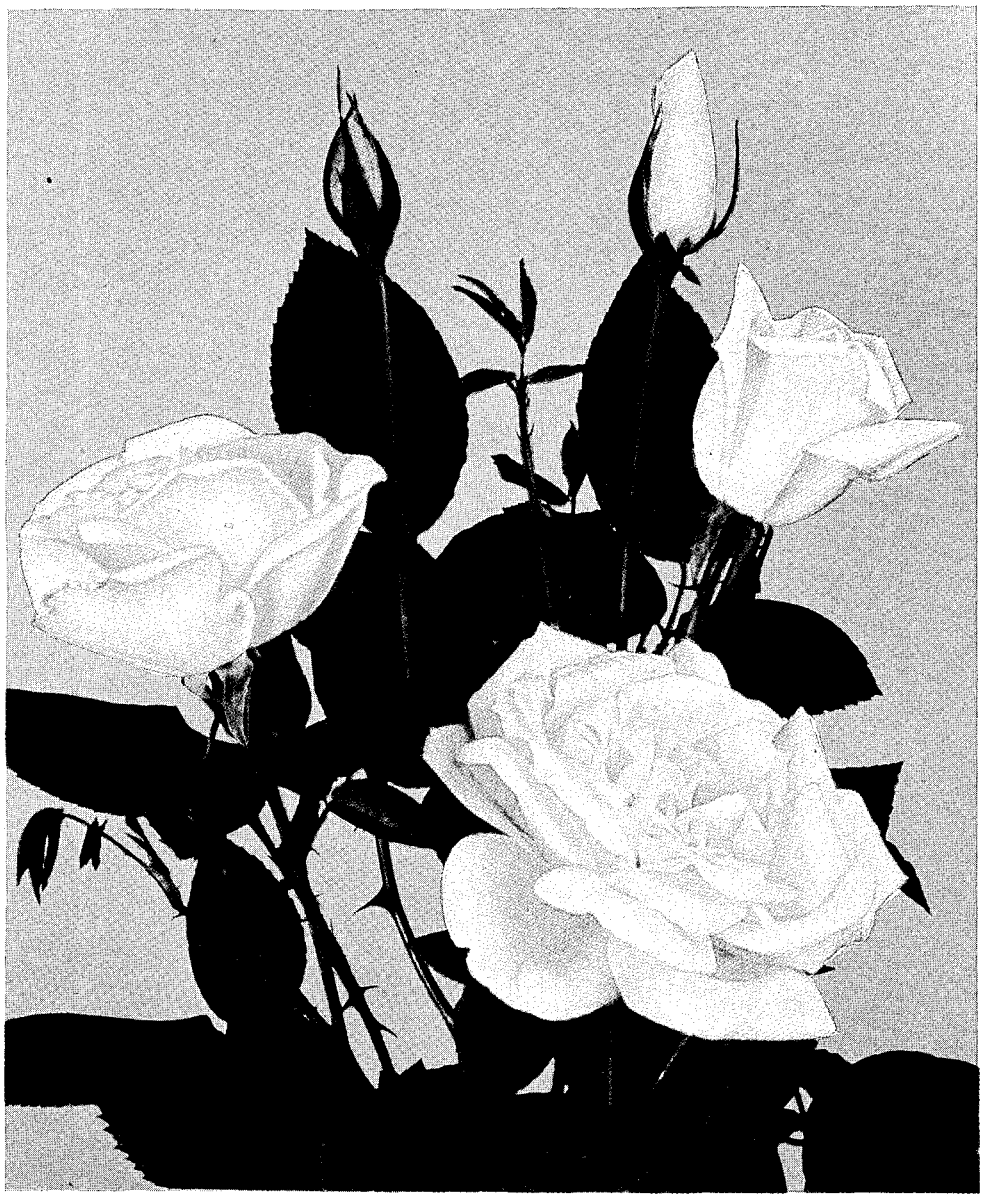
Inventor
Jean Gaujard
By Robb & Robb
Attorneys Patented Mar. 25, 1947

Plant Pat. 727

UNITED STATES PATENT OFFICE

727

ROSE PLANT

Jean Gaujard, Feyzin, France, assignor to Jackson & Perkins Company, Newark, N. Y., a corporation of New York Application June 26, 1943, Serial No. 492,467

1 Claim. (Cl. 47—61)

The present invention relates to a new and distinct variety of rose plant, originated by crossing two unnamed seedlings having promising characteristics, one of which came from the well known yellow rose "Pernet Ducher," and the other, a deep orange colored seedling which was also the pollen parent of the well known "Rose d'Or" (Plant Patent No. 482).

It is quite well known that "Pernet Ducher" is a very tall, vigorous growing yellow variety but lacks depth of color and therefore bleaches out to a very light color quickly. By hybridizing as above stated, a much improved, new variety was produced characterized by a deeper yellow color of the flower (Empire Yellow intensifying to Apricot Yellow in late fall), and a much more vigorous bush than the variety "Rose d'Or."

This new variety is further distinguished by its strong, spreading, bushy habit of growth, with foliage (old) of dark green color, tough, leathery texture having very pronounced veins; and new foliage of Mahogany Red.

Asexual reproduction shows that these characteristics hold true through succeeding propagations.

The following is a detailed description of this new variety, color terminology being in accord with Ridgway's Color Standard:

Parentage: Seedling.

*Seed parent.*—An unnamed seedling from "Pernet Ducher."

*Pollen parent.*—An unnamed seedling which was the pollen parent to "Rose d'Or."

Classification: Botanic and commercial—hybrid tea.

*Flower*

(Observations made in the fields of Jackson & Perkins Company, Newark, New York, in the morning of September 20, 1942.)

Blooming habit: Recurrent—continuous.

Bud:

*Size.*—Large.

*Form.*—Ovoid; is not affected by wet or hot weather.

*Color.*—When sepals first divide—Mustard Yellow, Plate 16; when petals begin to unfurl—Empire Yellow, Plate 4; when half blown—inside of petals, Empire Yellow, Plate 4, overcast with Pinard Yellow, Plate 4; reverse of petals, Pinard Yellow, Plate 4, overcast with Empire Yellow, Plate 4.

*Sepals.*—Branched; curl back when petals begin to unfurl. *Color*—outside—Oil Green, Plate 5; inside—Light Lumiere Green, Plate 17.

*Calyx.*—Shape—apple. Size—broad. Aspect—smooth. Color—Biscay Green, Plate 17.

*Peduncle.*—Length—long. Aspect—smooth. Color—Biscay Green, Plate 17. Strength—erect; heavy.

*Opening.*—Bud opens well; is not affected by adverse conditions.

Bloom:

*Size.*—Large. Average size when fully expanded, 5 to 5½ inches.

*Borne.*—Singly.

*Stems.*—Medium length; strong.

*Form.*—When first open—cupped. Permanence—retains its form to the end.

*Petalage.*—Double (full but open center). Number of petals under normal conditions, 25.

*Color.*—Center of flower—Pinard Yellow, Plate 4. Outer petals—lower half—Empire Yellow, Plate 4; upper half—Pinard Yellow, Plate 4. Base of petals (aiglet)—Lemon Chrome, Plate 4. Inside of petals—lower half—Empire Yellow, Plate 4; upper half—Pinard Yellow, Plate 4. Reverse of petals—Pinard Yellow, Plate 4. General tonality from a distance—Empire Yellow, Plate 4.

*Discoloration.*—General tonality at end of first day—Empire Yellow, Plate 4. Second day—between Empire Yellow, Plate 4, and Pinard Yellow, Plate 4. Third day—Pinard Yellow, Plate 4.

Petals:

*Texture.*—Thick; is not affected by wet or hot weather.

*Appearance.*—Inside—satiny; outside—shiny.

*Form.*—Oval.

*Arrangement.*—Imbricated (regularly arranged shinglelike). Petaloids in center—few; small.

*Persistence.*—Drop off cleanly.

*Fragrance.*—Slight. Nature—tea (average hybrid tea scent).

*Lasting quality.*—On the plant and as cut flower—long.

Genital organs:

*Stamens, anthers.*—Size—medium; many. Color—Light Cadmium, Plate 4. Arrangement—regular around styles.

*Stamens, filaments (threads).*—Length—medium. Color—Grenadine Red, Plate 2.

*Pollen.*—Buff Yellow, Plate 4.

*Styles.*—Columnar, uneven length; medium length; thin.

*Stigams.*—Grenadine Red, Plate 2.

*Ovaries.*—All enclosed in calyx.

*Plant*

Form: Bush.
Growth: Vigorous; branching.
Foliage: 5 to 7 leaflets.
*Size.*—Large.
*Quantity.*—Normal.
*Color.*—New foliage—upper side—Mahogany Red, Plate 2, mid-rib Oil Green, Plate 5; under side—Serpentine Green, Plate 16, with veining of Mahogany Red, Plate 1. Old foliage—Upper side—Dark Cress Green, Plate 31; under side—Light Cress Green, Plate 31. Shape—oval pointed.
*Texture.*—Upper side—leathery; under side—rough. Ribs and veins—prominent.
*Edge.*—Serrated (saw toothed).
*Serration.*—Single; deep.
*Rachis.*—Cress Green, Plate 31. Under side—smooth.
*Stipules.*—Medium length; smooth.
*Disease resistance.*—Resistant insofar as this is evidenced by absence of any disease throughout development and establishing of this variety.
Wood:
*New wood.*—Color—Hay's Russet, Plate 14. Bark—smooth.

*Old wood.*—Color—Cress Green, Plate 31. Bark—smooth.
Thorns (thorns are divided into thorns, prickles and short needles):
*Thorns.*—On main stalks from base—ordinary; on laterals from stalk—ordinary. Form—flat base; medium length, hooked downward. Color when young—Eugenia Red, Plate 13. Position—irregular.
*Prickles.*—On main stalks and on laterals—none.
*Short needles.*—On main stalks and on laterals—none.

I claim:

A new and distinct variety of rose plant of the hybrid tea class, characterized as to novelty by its strong, spreading, bushy habit of growth; old foliage of dark green color, tough leathery texture with pronounced veins; new foliage of Mahogany Red; and flowers of Empire Yellow in general tonality intensifying to Apricot Yellow in late fall, substantially as shown and described.

JEAN GAUJARD.